US007940966B2

(12) United States Patent  (10) Patent No.: US 7,940,966 B2
Yu et al.  (45) Date of Patent: *May 10, 2011

(54) FULL-FIELD BREAST IMAGE DATA PROCESSING AND ARCHIVING

(75) Inventors: Zengpin Yu, Palo Alto, CA (US); Shih-Ping Wang, Los Altos, CA (US)

(73) Assignee: U-Systems, Inc., Sunnyvale, CA (US)

( * ) Notice: Subject to any disclaimer, the term of this patent is extended or adjusted under 35 U.S.C. 154(b) by 1311 days.

This patent is subject to a terminal disclaimer.

(21) Appl. No.: 10/530,447

(22) PCT Filed: Nov. 25, 2003

(86) PCT No.: PCT/US03/37600
§ 371 (c)(1),
(2), (4) Date: Oct. 31, 2005

(87) PCT Pub. No.: WO2004/051405
PCT Pub. Date: Jun. 17, 2004

(65) Prior Publication Data
US 2006/0173303 A1  Aug. 3, 2006

Related U.S. Application Data

(63) Continuation-in-part of application No. 10/305,936, filed on Nov. 27, 2002, now Pat. No. 7,597,663, which is a continuation-in-part of application No. 10/160,836, filed on May 31, 2002, now Pat. No. 7,556,602, which is a continuation-in-part of application No. PCT/US01/43237, filed on Nov. 19, 2001.

(60) Provisional application No. 60/252,946, filed on Nov. 24, 2000.

(51) Int. Cl.
*G06K 9/00* (2006.01)

(52) U.S. Cl. ........................................ 382/128; 382/132

(58) Field of Classification Search .................. 382/128, 382/132
See application file for complete search history.

(56) References Cited

U.S. PATENT DOCUMENTS
3,556,081 A  1/1971  Jones
(Continued)

FOREIGN PATENT DOCUMENTS
DE  19753571 A1  6/1999
(Continued)

OTHER PUBLICATIONS

Bassett, L., "Automated and Hand-Held Breast US: Effect on Patient Management", Radiology 165, pp. 103-108 (1987).
(Continued)

*Primary Examiner* — John B Strege
(74) *Attorney, Agent, or Firm* — Cooper & Dunham, LLP

(57) ABSTRACT

A system, computer program product, and related methods are described for obtaining, processing, and/or and archiving full-field breast image data, such as full-field breast ultrasound (FFBU) data, in a manner that promotes ready integration with current x-ray mammogram-based breast cancer screening methodologies, and which can alternatively be used to support a full-field-only environment. Two-dimensional thick-slice images computed from a three-dimensional data volume are used to facilitate efficient archiving for a breast imaging session, the two-dimensional thick-slice images corresponding to slab-like subvolumes of the breast. Clinician data overload problems that can arise from the existence of large amounts of three-dimensional full-field breast image data are reduced. Archive space is also preserved while still providing sufficient information data for future reference purposes. Related adjunctive full-field workflow methods are also described. The described embodiments are applicable to FFBU imaging and other full-field breast imaging modalities such as MRI, CT, PET, and others.

21 Claims, 10 Drawing Sheets

U.S. PATENT DOCUMENTS

| | | |
|---|---|---|
| 3,765,403 A | 10/1973 | Brenden |
| 4,167,180 A | 9/1979 | Kossoff |
| 4,282,880 A | 8/1981 | Gardineer et al. |
| 4,298,009 A | 11/1981 | Mezrich et al. |
| 4,478,084 A | 10/1984 | Hassler et al. |
| 4,485,819 A | 12/1984 | Igl |
| 4,722,345 A | 2/1988 | Ueno et al. |
| 4,729,019 A | 3/1988 | Rouvrais |
| 4,796,632 A | 1/1989 | Boyd et al. |
| 4,930,143 A | 5/1990 | Lundgren et al. |
| 5,078,142 A | 1/1992 | Siczek et al. |
| 5,079,698 A | 1/1992 | Grenier et al. |
| 5,099,848 A | 3/1992 | Parker et al. |
| 5,133,020 A | 7/1992 | Giger et al. |
| 5,346,057 A | 9/1994 | Fisher et al. |
| 5,379,769 A | 1/1995 | Ito et al. |
| 5,396,890 A | 3/1995 | Weng |
| 5,413,211 A | 5/1995 | Faulkner |
| 5,433,202 A | 7/1995 | Mitchell et al. |
| 5,479,927 A | 1/1996 | Shmulewitz |
| 5,488,952 A | 2/1996 | Schoolman |
| 5,491,627 A | 2/1996 | Zhang et al. |
| 5,503,152 A | 4/1996 | Oakley et al. |
| 5,511,026 A | 4/1996 | Cleveland et al. |
| 5,603,326 A | 2/1997 | Richter |
| 5,640,956 A | 6/1997 | Getzinger et al. |
| 5,660,185 A | 8/1997 | Shmulewitz et al. |
| 5,662,109 A | 9/1997 | Hutson |
| 5,664,573 A | 9/1997 | Shmulewitz |
| 5,671,294 A | 9/1997 | Rogers et al. |
| 5,673,332 A | 9/1997 | Nishikawa et al. |
| 5,709,206 A | 1/1998 | Teboul |
| 5,729,620 A | 3/1998 | Wang |
| 5,734,384 A | 3/1998 | Yanof et al. |
| 5,776,062 A | 7/1998 | Nields |
| 5,779,641 A | 7/1998 | Hatfield et al. |
| 5,790,690 A | 8/1998 | Doi et al. |
| 5,803,082 A | 9/1998 | Stapleton et al. |
| 5,815,591 A | 9/1998 | Roehrig et al. |
| 5,820,552 A | 10/1998 | Crosby et al. |
| 5,828,774 A | 10/1998 | Wang |
| 5,833,627 A | 11/1998 | Shmulewitz et al. |
| 5,840,032 A | 11/1998 | Hatfield et al. |
| 5,851,180 A | 12/1998 | Crosby et al. |
| 5,865,750 A | 2/1999 | Hatfield et al. |
| 5,899,863 A | 5/1999 | Hatfield et al. |
| 5,904,653 A | 5/1999 | Hatfield et al. |
| 5,917,929 A | 6/1999 | Marshall et al. |
| 5,919,139 A | 7/1999 | Lin |
| 5,934,288 A | 8/1999 | Avila et al. |
| 5,935,071 A | 8/1999 | Schneider et al. |
| 5,938,613 A * | 8/1999 | Shmulewitz ................. 600/461 |
| 5,954,650 A | 9/1999 | Saito et al. |
| 5,964,707 A | 10/1999 | Fenster et al. |
| 5,983,123 A | 11/1999 | Shmulewitz |
| 5,984,870 A | 11/1999 | Giger et al. |
| 5,997,477 A | 12/1999 | Sehgal |
| 6,027,457 A | 2/2000 | Shmulewitz et al. |
| 6,029,797 A | 2/2000 | Olsson |
| 6,035,056 A | 3/2000 | Karssemeijer |
| 6,059,727 A | 5/2000 | Fowlkes et al. |
| 6,068,597 A | 5/2000 | Lin |
| 6,075,879 A | 6/2000 | Roehrig et al. |
| 6,091,841 A | 7/2000 | Rogers et al. |
| 6,102,861 A | 8/2000 | Avila et al. |
| 6,102,866 A | 8/2000 | Nields et al. |
| 6,117,080 A | 9/2000 | Schwartz |
| 6,123,733 A | 9/2000 | Dalton |
| 6,155,978 A | 12/2000 | Cline et al. |
| 6,157,697 A | 12/2000 | Mertelmeier et al. |
| 6,178,224 B1 | 1/2001 | Polichar et al. |
| 6,181,769 B1 | 1/2001 | Hoheisel et al. |
| 6,190,334 B1 | 2/2001 | Lasky et al. |
| 6,198,838 B1 | 3/2001 | Roehrig et al. |
| 6,237,750 B1 | 5/2001 | Damkjaer et al. |
| 6,246,782 B1 | 6/2001 | Shapiro et al. |
| 6,254,538 B1 | 7/2001 | Downey et al. |
| 6,263,092 B1 | 7/2001 | Roehrig et al. |
| 6,266,435 B1 | 7/2001 | Wang |
| 6,269,565 B1 | 8/2001 | Inbar et al. |
| 6,277,074 B1 | 8/2001 | Chaturvedi et al. |
| 6,278,793 B1 | 8/2001 | Gur et al. |
| 6,282,305 B1 | 8/2001 | Huo et al. |
| 6,301,378 B1 | 10/2001 | Karssemeijer et al. |
| 6,311,419 B1 | 11/2001 | Inbar |
| 6,317,617 B1 | 11/2001 | Gilhuijs et al. |
| 6,334,847 B1 | 1/2002 | Fenster et al. |
| 6,377,838 B1 | 4/2002 | Iwanczyk et al. |
| 6,385,474 B1 | 5/2002 | Rather et al. |
| 6,396,940 B1 | 5/2002 | Carrott et al. |
| 6,413,219 B1 | 7/2002 | Avila et al. |
| 6,450,962 B1 | 9/2002 | Brandl et al. |
| 6,459,925 B1 | 10/2002 | Nields et al. |
| 6,461,298 B1 | 10/2002 | Fenster et al. |
| 6,524,246 B1 | 2/2003 | Kelly et al. |
| 6,530,885 B1 | 3/2003 | Entrekin et al. |
| 6,574,499 B1 | 6/2003 | Dines et al. |
| 6,628,815 B2 | 9/2003 | Wang |
| 6,630,937 B2 | 10/2003 | Kallergi et al. |
| 6,636,584 B2 | 10/2003 | Johnson et al. |
| 6,682,484 B1 | 1/2004 | Entrekin et al. |
| 6,876,879 B2 | 4/2005 | Dines et al. |
| 6,909,792 B1 | 6/2005 | Carrott et al. |
| 7,103,205 B2 * | 9/2006 | Wang et al. ................. 382/132 |
| 7,313,260 B2 | 12/2007 | Wang et al. |
| 2002/0173722 A1 | 11/2002 | Hoctor et al. |
| 2003/0000810 A1 | 1/2003 | Hansen et al. |
| 2003/0007598 A1 | 1/2003 | Wang et al. |
| 2003/0015406 A1 | 1/2003 | Guldenfels et al. |
| 2003/0181801 A1 | 9/2003 | Lasser et al. |
| 2003/0194121 A1 | 10/2003 | Eberhard et al. |
| 2003/0212327 A1 | 11/2003 | Wang et al. |
| 2004/0015080 A1 | 1/2004 | Kelly et al. |
| 2004/0181152 A1 | 9/2004 | Zhang et al. |
| 2004/0254464 A1 | 12/2004 | Stribling |
| 2005/0113683 A1 | 5/2005 | Lokhandwalla et al. |
| 2005/0171430 A1 | 8/2005 | Zhang et al. |

FOREIGN PATENT DOCUMENTS

| | | |
|---|---|---|
| DE | 19902521 A1 | 7/2000 |
| EP | 0882426 | 12/1998 |
| EP | 0730431 | 3/2000 |
| JP | 2003-310614 | 11/2003 |
| WO | WO83/02053 A1 | 6/1983 |
| WO | WO94/21189 | 9/1994 |
| WO | WO02/17792 | 3/2002 |
| WO | WO03/103500 A1 | 12/2003 |
| WO | WO2004/064644 A1 | 8/2004 |

OTHER PUBLICATIONS

Buchberger, W., et al., "Incidental Findings on Sonography of the Breast: Clinical Significance and Diagnostic Workup", American Journal of Radiology (AJR) 173, pp. 921-927 Oct. 1999.

Carson, P. et al., "Lesion Detectability in Ultrasonic Computed Tomography of Symptomatic Breast Patients", Investigative Radiology, vol. 23, No. 6, pp. 421-427, Jun. 1998.

Chen et al., "Computer-aided Diagnosis Applied to US of Solid Breast Nodules by Using Neural Networks", Radiology, pp. 407-412, Nov. 1999.

Cheng et al., "Automated Detection of Breast Tumors in Ultrasonic Images Using Fuzzy Reasoning", Proceedings of the IEEE Computer Society International Conference on Image Processing vol. III, pp. 420-423, Oct. 26-29, 1997.

Dawant, Benoit M. et al., "Image Segmentation", Handbook of Medical Imaging, vol. 2; Medical Image Processing and Analysis, Sonka and Fitzpatrick, eds., Chapter 2, pp. 98-101, SPIE Press, 2000.

Giger et al., "Computer-Aided Diagnosis in Mammography", Handbook of Medical Imaging, vol. 2: Medical Image Processing and Analysis, Sonka and Fitzpatrick, Chapter 15, pp. 915-1004, SPIE Press 2000.

Heywang-Kobrunner, Dershaw and Schreer, Diagnostic Breast Imaging, pp. 87-102, Thieme Publishers 2001.

Jackson, Valerie P., "Controversies in Ultrasound Screening", Society of Breast Imaging 5th Postgraduate Course, May 16-19, 2001, Sheraton Harbor Island, San Diego, CA, pp. 93-95, May 16, 2001.

Jalali, "Sound Combination: Ultrasound Paired With Mammography Can Improve Cancer Detection for Dense-Breasted Women", ADVANCE for Administrators in Radiology and Radiation Oncology, pp. 68-70, Mar. 1999.

Kopans, D. et al., "Whole-Breast US Imaging: Four Year Follow-Up", Radiology 157: 505-507, 1985.

Kopans, "Breast Cancer Screening With Ultrasonography", Lancet, vol. 354, pp. 2096-2097, Dec. 18/25, 1999.

Labsonics, Inc., "LABSONICS Ultrasound Breast Scanner: Accurate, High-Performance Investigation of the Breast for Confident Diagnosis", 8-page product brochure from LABSONICS, Inc., Mooresville, Indiana, 1983.

Lehman et al., "Effect of Age and Breast Density on Screening Mammograms with False-Positive Findings", American Journal of Radiology (AJR) 173: 1651-1655, Dec. 1999.

LORAD, a Hologic Company, "Fully Automatic Self-Adjusting Tilt Compression Plate", 3-page product description downloaded and printed on May 22, 2002 from www.loradmedical.com/p225.html.

Lowers, J., "Experimental Modes Abound for Detecting Breast Cancer: Vibrational Resonance Technique Among the Contenders", Women's Health Supplement to Diagnostic Imaging, pp. 15-17, Apr. 2001.

McKnoulty, L., "Ultrasound has Unique Strengths In Breast Imaging", 3-page printout from www.auntminnie.com one Mar. 1, 2002, Jan. 2002.

McSweeney, M. et al., "Whole Breast Snongraphy," Radiologic Clinics of North America, vol. 23, No. 1, pp. 157-167, Mar. 1985.

Mendelson, Ellen B., "Current Status of Breast US", RSNA Categorical Course in Breast Imaging, pp. 295-309, 1999.

Qayyum, A. et al., "MR Imaging Features of Infiltrating Lobular Carcinoma of the Breast: Histopathologic Correlation", American Journal of Radiology (AJR) 178: 1227-1232, May 2002.

Rahbar, G. et al., "Benign Versus Malignant Solid Breast Masses: US Differentiation", Radiology 213:889-894, 1999.

Rapp, Cynthia L., "Breast Ultrasound", Lecture Notes for EDA AHP 230-0406, Health & Sciences Television Network, Primedia Healthcare, Carrolton TX, Mar. 2000.

Richter, K. et al., "Quantitative Parameters Measured by a New Sonographic Method for Differentiation of Benign and Malignant Breast Disease", Investigative Radiology, vol. 30, No. 7, pp. 401-411, Jul. 1995.

Richter, K. et al., "Detection of Diffuse Breast Cancers with a New Sonographic Method", J. Clinical Ultrasound 24: pp. 157-168, May 1996.

Richter, K. et al., "Differentiation of Breast Lesions by Measurements Under Craniocaudal and Lateromedial Compression Using a New Sonographic Method", Investigative Radiology, vol. 31, No. 7, pp. 401-414, Jul. 1996.

Richter, K. et al., "Description and First Clinical Use of a New System for Combined Mammography and Automated Clinical Amplitude/Velocity Reconstructive Imaging Breast Sonography", Investigative Radiology, vol. 32, No. 1, pp. 19-28, Jan. 1997.

Richter, K. et al., "Detection of Malignant and Benign Breast Lesions with an Automated US System: Results in 120 Cases", Radiology 205: pp. 823-830, Dec. 1997.

Russ, "The Image Processing Handbook, $3^{rd}$ Edition", CRC Press/IEEE Press, p. 264, 1998.

Schreiman, J. et al., "Ultrasound Transmission Computed Tomography of the Breast", Radiology 150; pp. 523-530, 1984.

Singh, S. and Al-Mansoori, R., "Identification of Regions of Interest in Digital Mammograms", J. Intelligent Systems10:2, 2000.

Smith, D., "Breast Ultrasound", Radiologic Clinics of North America, vol. 39, No. 3, pp. 485-497, May 2001.

"Ultrasound RSNA Preview: Productivity and Ease of Use Dominate New Ultrasotind Productss", Medical Imaging, pp. 55-56, Nov. 1999.

Zonderland, H. et al., "Diagnosis of Breast Cancer: Contribution of US as an Adjunct of Mammography", Radiology 213: 413-422, 1999.

Medison Image Gallery, five (5) selected pages from www.medison.com, printed Oct. 10, 2001.

Foster, F.S. et al., "The Ultrasound .Macroscope: Initial Studies of Breast Tissue", Ultrasonic Imaging USA, vol. 6, No. 3, Jul. 1984, pp. 243-261.

European Search Report dated Jan. 29, 2007 in connection with counterpart European patent application No. 03 73 4336.

Dec. 28, 2005 International Search Report and Written Opinion in connection with International Application No. PCT/US05/19604.

International Search Report in PCT/US03/37600.

* cited by examiner

US 7,940,966 B2

FULL-FIELD BREAST IMAGE DATA PROCESSING AND ARCHIVING

CROSS-REFERENCE TO RELATED APPLICATIONS

This application is a continuation-in-part of U.S. Ser. No. 10/305,936 filed Nov. 27, 2002 now U.S. Pat. No. 7,597,663, which is a continuation-in-part of U.S. Ser. No. 10/160,836 filed May 31, 2002 now U.S. Pat. No. 7,556,602, which is a continuation-in-part of International Application Ser. No. PCT/US01/43237, filed Nov. 19, 2001, which claims the benefit of U.S. Provisional Application No. 60/252,946 filed Nov. 24, 2000, each of the above being incorporated by reference herein.

FIELD

This patent specification relates to full-field imaging of the breast. More particularly, this patent specification relates to systems, computer program products, and related methods for presenting, manipulating, annotating, and/or archiving full-field breast image information such as full-field breast ultrasound information.

BACKGROUND

The ongoing disconnect between the possible and the practical is especially visible in the medical sciences field where, at one end, sophisticated research and development efforts continue to advance the frontiers of disease prevention and lifespan extension while, at the other end, governments and insurers continue to struggle with providing a reasonable standard of care at a manageable cost to an aging population. The medical imaging field offers an example of this disconnect. Sophisticated imaging devices and associated computer algorithms have been developed that can produce gigabytes of high-quality images of a patient's interior anatomy. However, cost-pressured hospitals and time-pressured clinicians are justifiably resistant to adopting a standard of care for disease screening that would add yet another modality to clinical workflow and hold clinicians accountable for large amounts of additional image data per patient. In the practical world of medical imaging, it is possible for a proposed screening modality to fail simply because it provides "too much information" to the clinician.

Breast cancer is the most common cancer among women other than skin cancer, and is the second leading cause of cancer death in women after lung cancer. For the year 2003, the American Cancer Society estimates about 211,300 new invasive cases of breast cancer and 39,800 deaths from breast cancer among women in the United States. X-ray mammography is currently the only imaging method for mass breast cancer screening. In health maintenance organizations (HMOs) and other medical organizations, specialized x-ray mammography clinics designed for high patient throughput are being increasingly used to screen as many women as possible in a time and cost efficient manner. Numerous studies have shown that early detection saves lives and increases treatment options.

As discussed in Ser. No. 10/160,836, supra, it has been found that the use of ultrasound mammography (sonomammography) in conjunction with conventional x-ray mammography can drastically increase the early breast cancer detection rate. Whereas x-ray mammograms only detect a summation of the x-ray opacity of individual slices over the entire breast, ultrasound can separately detect the sonographic properties of individual slices of breast tissue, and therefore may assist the radiologist in detecting breast lesions where x-ray mammography alone fails.

Although primarily described infra in the context of ultrasound imaging, it is to be appreciated that data from other full-field breast imaging modalities (e.g., MRI, CT, PET) can be advantageously processed and/or archived according to one or more of the preferred embodiments described herein. As used herein, the term "radiologist" generically refers to a medical professional, clinician, or similar person that analyzes medical images and makes clinical determinations therefrom, it being understood that such person might be titled differently, or might have varying qualifications, depending on the country or locality of their particular medical environment, or depending on the particular imaging modality being used.

One of the problems involved in integrating a full-field modality such as ultrasound into existing breast cancer screening environments relates generally to clinical workflow. Generally speaking, it is neither time-efficient nor cost-efficient to perform an adjunctive full-field breast ultrasound (FFBU) scan on every patient. However, it is likewise not efficient to perform FFBU screening on an ad hoc basis, for example, in which patients would get called back to the screening clinic for an FFBU only when the radiologist or other clinician analyzing their x-ray mammogram determines that an FFBU procedure is required. It would be desirable to provide a method and related systems for streamlining the x-ray mammography/FFBU patient visit workflow so as to jointly use the x-ray mammography equipment, the FFBU equipment, and the associated clinical staff time in an efficient manner.

Another problem involved in integrating a full-field breast imaging modality into existing breast cancer screening environments relates generally to archiving the full-field image data, such as full-field breast ultrasound data, in addition to the x-ray mammogram data. A most complete archive would comprise an entire three-dimensional volume of ultrasound data. However, this three-dimensional ultrasound dataset is generally much more voluminous than the traditional x-ray mammogram data, e.g., on the order of gigabytes for the complete ultrasound volume as compared to tens of megabytes for complete x-ray mammogram data. Regardless of whether the information would be stored in a totally digital archive, a hybrid digital/hardcopy archive, or a purely hardcopy archive, storage space would become a problem. Additionally, other problems can arise relating to the storage of the entire ultrasound data volume, such as the possibility for subsequent malpractice claims involving unfair hindsight analyses of the entire ultrasound data volume.

In view of the above discussions, it would be desirable to provide methods and associated systems for obtaining, processing, and/or and archiving full-field breast image data, such as full-field breast ultrasound (FFBU) data, in a manner that promotes ready integration with current x-ray mammogram-based breast cancer screening methodologies.

It would be desirable to provide such methods and associated systems for full-field breast imaging that avoids or reduces clinician data overload problems that can arise from the existence of large amounts of three-dimensional full-field breast image data.

It would be still further desirable to provide such methods and associated systems that reduce required archive space for full-field breast image data while still providing sufficient data for future analysis or comparison purposes.

SUMMARY

A system, computer program product, and related methods are provided for processing a three-dimensional data volume representing at least one physical property of a breast obtained during a breast imaging session, wherein two-dimensional thick-slice images computed from the three-dimensional data volume are used to facilitate efficient archiving of the at least one physical property for that breast imaging session, the two-dimensional thick-slice images corresponding to slab-like subvolumes of the breast. According to a preferred embodiment, the two-dimensional thick-slice images are archived such that archiving of the entire three-dimensional data volume is not required, thereby preserving data storage space and associated resources while still providing an archival dataset sufficient for future reference purposes. Although described herein in the context of full-field breast ultrasound (FFBU) imaging, it is to be appreciated that the features and advantages of the preferred embodiments are applicable for a variety of other full-field breast imaging modalities such as MRI, CT, PET, etc.

According to one preferred embodiment, the slab-like subvolumes associated with the thick-slice images have an average thickness corresponding to a lesion size to be detected according to the FFBU imaging modality. Preferably, the slab-like subvolumes collectively occupy substantially all of a clinically relevant portion of the breast volume, and the archival dataset comprises each of the thick-slice images, but does not include the original three-dimensional data volume. Storage space is preserved because the collection of thick-slice images is a smaller set of data than the original three-dimensional data volume, and archival utility is maintained because the slab thickness is small enough to capture the lesion size to be detected.

Preferably, the thick-slice images maintained in the archival dataset are the same thick-slice images that are viewed by a viewer, such as a radiologist, during a viewing session. User interface tools are provided to allow the viewer to annotate the thick-slice images, view planar and/or "raw" ultrasound slices corresponding to selected locations on the thick-slice images, conveniently zoom to regions of interest, and allow other convenient and useful analysis activities. Optionally, planar ultrasound slices corresponding to selected locations of interest may be included in the thick-slice archival dataset. In one preferred embodiment, the radiologist may select a particular point on a thick-slice image, such as the center of a possible density, to instantiate a real-time segmentation and volume computation, the display unit thereafter highlighting the segmented lesion on the display and presenting the volume result to the viewer. In another preferred embodiment, the radiologist may view and provide annotations related to markers automatically generated by a computer-aided diagnosis (CAD) system that has processed the three-dimensional data volume, the thick-slice images, and/or the associated x-ray mammogram data. Annotations, marks, and any of a variety of other viewer inputs are then archived in a manner that associates them with the thick-slice image archival dataset.

According to another preferred embodiment, a system, computer program product, and related methods are provided for facilitating workflow in an x-ray mammography screening environment such that integration of an adjunctive full-field breast imaging modality, such as FFBU, can be achieved with reduced marginal cost and, in some cases, can even lower overall screening costs. Prior to a patient's visit to an x-ray mammogram clinic, previously recorded medically-relevant information for that patient is accessed for determining whether that patient should be scheduled for x-ray mammogram alone versus the combination of x-ray mammogram and FFBU scan. If the combination x-ray mammogram and FFBU scan is indicated, a scheduler generates an appointment and allocates clinic resources such that the x-ray mammogram and the FFBU scan take place on the same patient visit. The previously recorded medically-relevant information may include archived x-ray image data, archived FFBU image data, patient history, family history, and social/demographic information.

DETAILED DESCRIPTION

Figure 1:
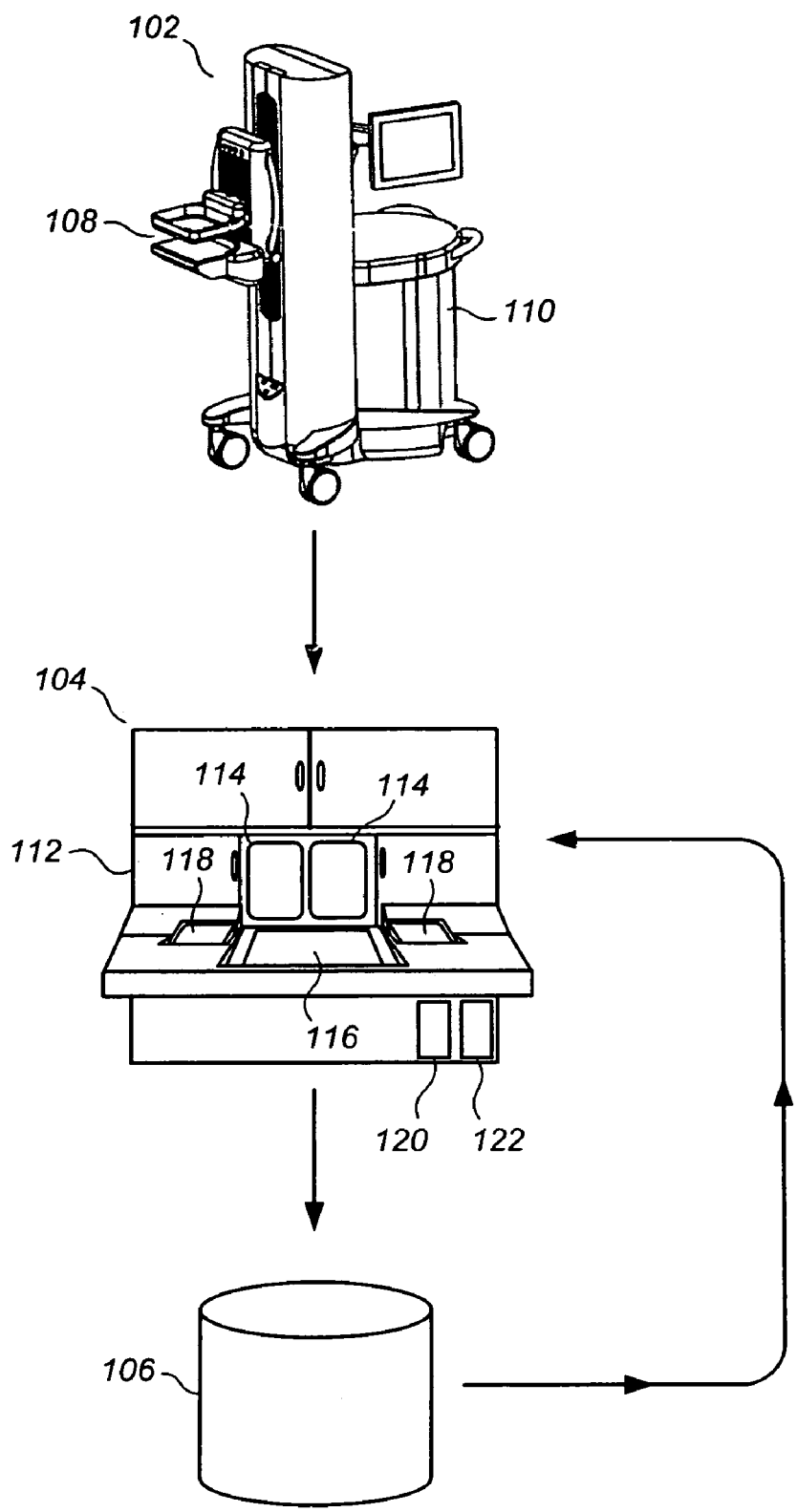
FIG. 1 illustrates a conceptual view of a breast cancer screening system according to a preferred embodiment.

FIG. 1 illustrates a conceptual view of a breast cancer screening system according to a preferred embodiment comprising a full-field breast ultrasound (FFBU) scanner 102, a viewing workstation 104, and an archive 106. In one preferred embodiment, the breast cancer screening system of FIG. 1 is adjunctive to an x-ray mammography system, although in an alternative preferred embodiment, FFBU imaging is used as a sole basis for breast cancer screening. While the latter preferred embodiment affords an advantage that there are no x-ray radiation dangers, it is to be appreciated that using ultrasound as a sole breast cancer screening modality is not yet approved by the FDA in the United States or other known governmental authority. Nevertheless, another appealing feature of the latter preferred embodiment is that, because FFBU scanning can usually involve less extreme breast compression than x-ray mammography, e.g., 8 pounds as compared to 20 pounds or more, it affords a further potential advantage that more women might be willing to get screened more often because there is less pain involved in the procedure.

The FFBU scanner 102 is similar to that described in PCT/US03/31434 filed Oct. 1, 2003, which is incorporated by reference herein, and performs full-field imaging of the breast to obtain a three-dimensional data volume corresponding to sonographic properties of the breast tissue. The patient's breast is placed in a compression and scanning assembly 108 that, in conjunction with an FFBU processor 110, scans the breast such that a three-dimensional data volume is generated. Preferably, the breast is compressed along a standard x-ray mammogram plane such as the craniocaudal (CC) or mediolateral oblique (MLO) plane, or other plane used in the associated x-ray mammograms preferably being taken on the same office visit. However, the scope of the preferred embodiments is not so limited to these x-ray compression planes.

The FFBU processor 110 and/or another computer coupled to receive data therefrom then processes the three-dimensional data volume to generate a plurality of two-dimensional thick-slice images corresponding to slab-like subvolumes of the breast. Preferably, each of the slab-like subvolumes is parallel to a standard x-ray mammogram plane, although the scope of the preferred embodiments is not so limited. For clarity of description herein, the y-axis represents the head-to-toe direction with respect to the patient, the x-axis represents the left-to-right direction, and the z-axis extends outward from the chest wall. The x-y, y-z, and x-z planes thus correspond to the coronal, sagittal, and axial planes, respectively. Thus, by way of example, thick-slice images corresponding to a CC view, for which the breast was scanned while compressed along an x-z (axial) plane, would correspond to slab-like subvolumes substantially parallel to the x-z (axial plane), the slab-like volumes extending vertically in the "y" direction by an amount that can be referred to as their slab thickness or thick-slice thickness. Preferably, the thick-slice images are computed according to one or more of the methods described in one or more of the above incorporated applications, and/or the commonly assigned U.S. Ser. No. 60/439,437, filed Jan. 9, 2003, and/or the commonly assigned U.S. Ser. No. 10/305,661, filed Nov. 27, 2002, each of which is incorporated by reference herein.

Preferably, the collection of slab-like volumes, each having a corresponding two-dimensional thick-slice image, collectively occupy substantially all of a clinically relevant portion of the breast volume. In such arrangement, displaying all of the thick-slice images to the viewer can allow for a fast appreciation of structures in the breast, or lack thereof, while at the same time not requiring the viewer to slog through each slice used to generate the three-dimensional data volume. The clinically relevant portion of the breast volume refers to the portion of the breast volume imaged by the full-field imaging system that is generally recognized to be locations where breast cancer can occur. Thus, for example, areas very close to the skinline might be considered as not clinically relevant. As another example, the interior portions of silicone breast implants may also be considered as not clinically relevant because there is no living tissue present.

The viewing workstation 104, which is similar to that described in Ser. No. 10/305,936, supra, provides an interactive display and associated user interface for viewing, analyzing, and annotating FFBU data in conjunction with x-ray mammography data. In an FFBU-only environment, the portions dedicated to displaying x-ray mammogram data can be omitted or replaced by further display devices allowing further simultaneous views of the FFBU data. Viewing workstation 104 comprises an x-ray mammogram display 112 for allowing display of x-ray mammograms 114. Although shown as a film-based unit in FIG. 1, the x-ray mammogram display 112 can alternatively comprise an all-digital workstation in a digital mammography environment. The viewing workstation 104 can be conformed to various standards for picture archiving and retrieval (PACS) such as those described in the DICOM standard (Digital Imaging and Communications in Medicine) defined and maintained by the National Electrical Manufacturers Association.

Viewing workstation 104 further comprises a full-sized LCD display 116 and two CRT displays 118 for viewing the FFBU thick-slice data in conjunction, if necessary, with planar ultrasound slices derived from the FFBU scans. As described in Ser. No. 10/305,936, supra, although many different display arrangements may be used, one preferred method is to use CRT displays to display planar ultrasound data and the LCD displays to display the thick-slice images. Computer-aided diagnosis (CAD) markers may be provided in conjunction with the FFBU thick-slice data and/or the x-ray mammogram data.

Viewing workstation 104 further comprises a user interface processor 120 for receiving viewer inputs and driving the displays 116-118. Any of a variety of user interface devices (not shown) can be provided in accordance with the preferred embodiments, ranging anywhere from simple a keyboard/mouse arrangement, to foot-pedal and touch-screen display arrangements, all the way to highly exotic user interface methods based on voice-actuated inputs, retinal tracking inputs, heads-up displays, lenticular displays, virtual reality displays, holographic displays, stereotactic displays, forced-mechanical-feedback displays, and audible-annotation displays.

Viewing workstation 104 further comprises an archiving processor 122 in communication with the FFBU scanner 102 and/or the user interface processor 120 configured and adapted for achieving the archiving functionalities described herein. Although the particular hardware arrangement of FIG. 1 represents one preferred system, it is to be appreciated that the functionalities of the FFBU processor 110, user interface processor 120, and archive processor 122 can be allocated, separated, integrated, and/or tiered in a variety of different ways that achieve the functionalities described herein without departing from the scope of the preferred embodiments. By way of example, a single stand-alone processor separate from the FFBU scanner 102 and viewing station 104 (connected to them across a LAN, MAN, or WAN network, for example) can be substituted for the separate hardware elements 110, 120, and 122. By way of further example, the display processor 120 can be programmed to perform thick-slice generation, user interface functions, CAD functions, and archiving functions by itself, and so on.

Archive 106 is coupled generally to viewing workstation 104, and particularly to archive processor 122, for receiving and storing an archival dataset for long-term storage purposes or for other future reference. It is to be appreciated that the archive 106, although shown iconically as a computer hard disk, can comprise any tangible storage medium capable of storing two-dimensional image data. Examples include paper, film, magnetic disk, optical disk, magnetic tape, and non-volatile integrated circuit memory. Thus, for example, the archive processor 122 can be coupled to a DICOM-compliant printer, for example, which prints the archival dataset onto paper or film, and then the paper or film is carried over to a physical drawer or stack for long-term storage.

One special advantage according to a preferred embodiment is backward-compatibility way with today's existing two-dimensionally-based infrastructure, because the preferred FFBU archive datasets are two-dimensional in nature, intended to be shown in a two-dimensional manner, and generally not intended for three-dimensional reconstruction. Thus, for example, in a film-based x-ray mammogram environment in which the films are stored in physical drawers and stacks, the two-dimensional FFBU archive data can be easily transferred to one or two sheets of film or paper and slipped into the same file as the x-ray mammogram film. In other preferred embodiments there may be more than two sheets of film or paper, e.g., 3-10 sheets, but generally there will not be so many sheets as to be cumbersome. This is to be contrasted with the mass archiving of the entire three-dimensional data volume which, if printed out to paper or film, would require hundreds of sheets or more.

It is to be appreciated, however, that the archive 106 is not limited to storing single flat-file records containing printouts or digital/digitized versions of the drawings described infra. For example, the preferred embodiments are readily implemented in a totally paperless and filmless environment as well, and in such cases the archive 106 will usually comprise a distributed database architecture consistent with most modern PACS systems. The various distributed elements composing the archive 106 can segregate, aggregate, index, and allocate the archival datasets described herein without departing from the scope of the preferred embodiments. For example, the different components (text comments, 2-D images, and annotations) can all be digitally stored in different places, and even on different machines or networks, and then associated with hyperlinks. In one preferred embodiment, the archive 106 is implemented in a DICOM-compliant data communications and storage architecture.

As indicated by the arrows in FIG. 1, the FFBU scanner 102 forwards the FFBU data to the viewing workstation 104 and, upon review, assessment, annotation, and the creation of an archival dataset, the archival dataset is transferred to the archive 106. During a subsequent screening process—for example, during next year's review process for the patient—the archival dataset can be retrieved from the archive 106 for comparison, if necessary, to the new FFBU and/or x-ray data. This is useful, for example, for ensuring that a fibroadenoma identified in year "N" does not get any larger in year "N+1."

It is to be appreciated that some data collected from outside the viewing station 104 can be included in the archival dataset without departing from the scope of the preferred embodiments. By way of example, radiologists often prefer speaking into a voice recorder and making an audio tape of their comments and assessments, which are later dictated into ASCII text. This text data can be readily included into the archival dataset without departing from the scope of the preferred embodiments.

Figure 2:
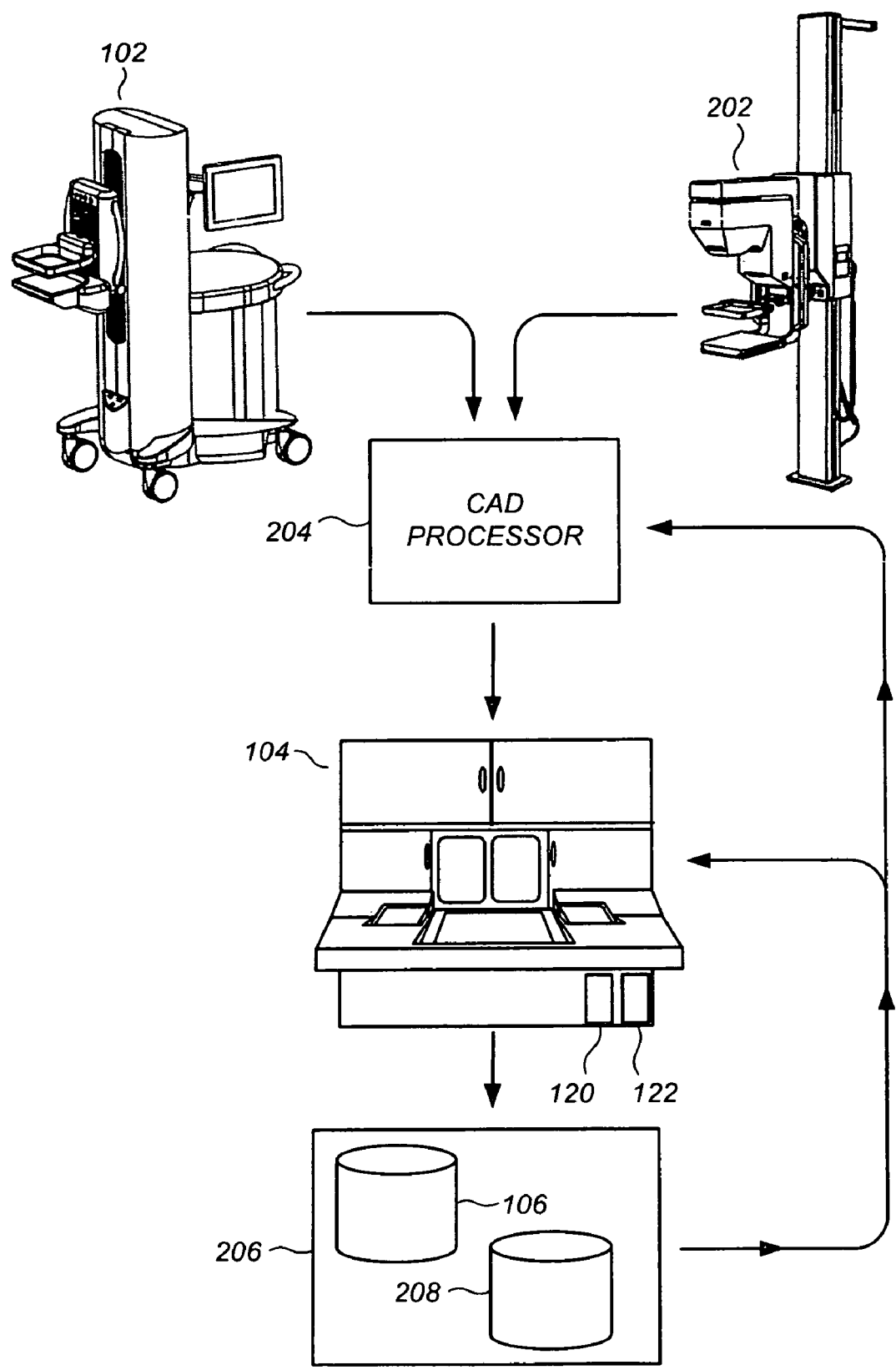
FIG. 2 illustrates a conceptual view of a breast cancer screening system according to a preferred embodiment.

FIG. 2 illustrates a conceptual view of a breast cancer screening system according to a preferred embodiment in which FFBU data is used in conjunction with x-ray mammogram screening. In this preferred embodiment, x-ray mammogram data derived from an x-ray mammogram unit 202 and adjunctive FFBU derived from FFBU scanner 102 are provided to a CAD processor 204 that automatically identifies anatomical abnormalities in the breast tissue. Annotation road maps and/or other abnormality identifying information is provided to the viewing workstation 104. An archival dataset comprising the x-ray mammogram data, the FFBU thick-slice data, the CAD annotations, and the viewer annotations is transferred to an overall archive 206 including an archive 106 for storing the FFBU thick-slice data and annotations related thereto, and an archive 208 for storing the x-ray mammogram data and annotations related thereto. As indicated by the arrows in FIG. 2, both the CAD processor 204 and the viewer can advantageously use the archived data for abnormality detection and assessment purposes.

According to one preferred embodiment, viewing workstation 104 including archive processor 122 is configured to prevent the viewer from removing any automatically-obtained CAD markers from the FFBU dataset or the x-ray mammogram dataset. For quality control purposes, this will urge the viewer to enter comments for every automatically-obtained CAD marker, even clearly-false positives, instead of simply erasing or deleting that marker. For example, this is expected to be useful because the FFBU data, including the thick-slice images, can help the viewer rapidly identify obviously-false positives in the x-ray CAD system outputs. Since these markers are clearly without merit it would be tempting to simply erase or delete them. However, for overall quality-control purposes and for other practical reasons, may be better that all CAD markers, even the obviously false positives, are retained.

Figure 3:
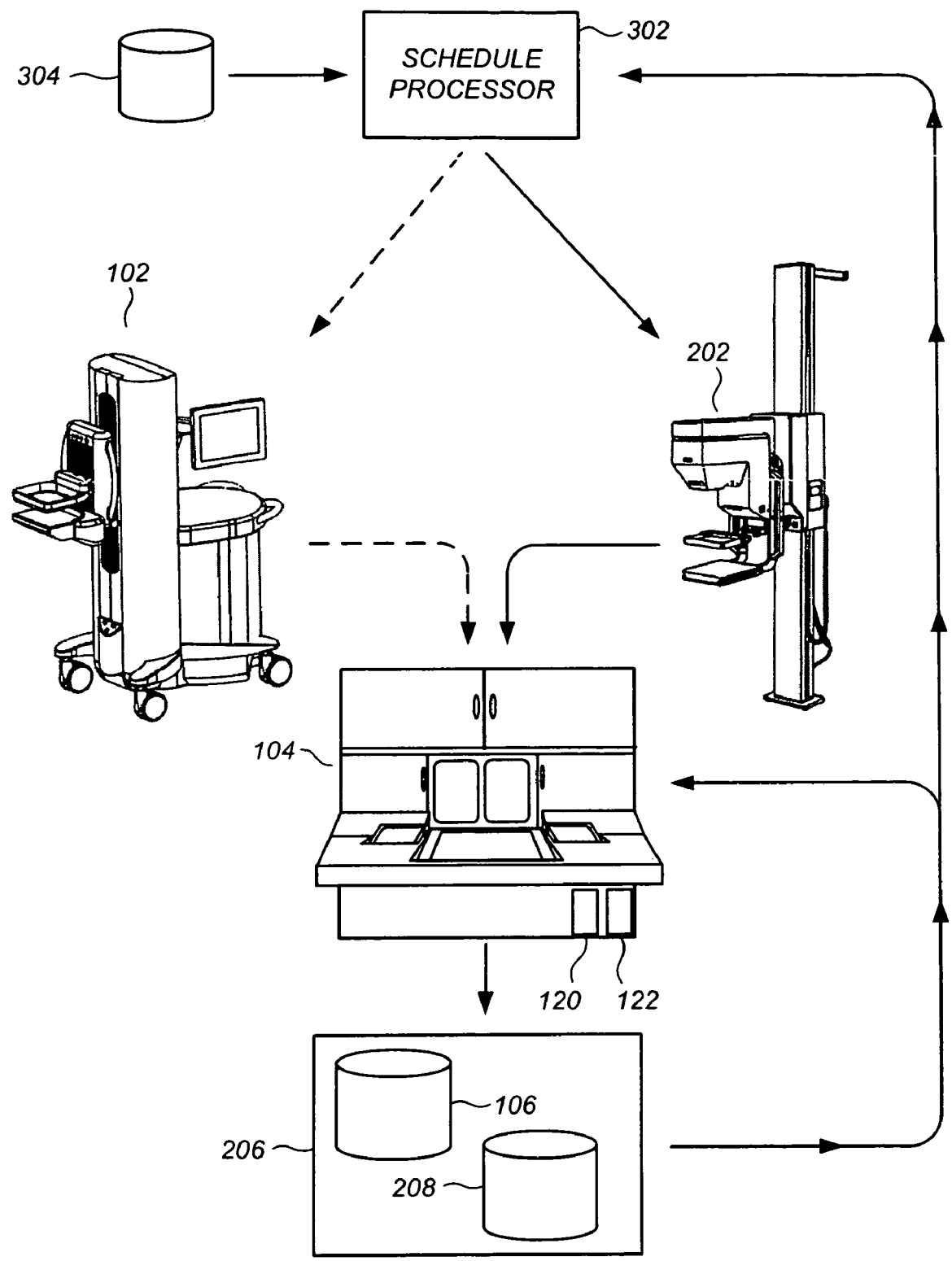
FIG. 3 illustrates a conceptual workflow in a breast cancer screening environment according to a preferred embodiment.

FIG. 3 illustrates a conceptual view of a workflow system in a breast cancer screening environment according to a preferred embodiment. A schedule processor 302 and a medical information database 304 are used in conjunction with the system of FIG. 2 (reproduced without the CAD processor for space purposes in FIG. 3) for reducing marginal cost that may be incurred in an x-ray mammogram screening clinic when augmented with FFBU capability and, in some cases, even lowering overall screening costs.

It has been found that FFBU screening according to the present and commonly assigned incorporated applications is highly amenable to standardization and the development of predetermined FFBU qualifying requirements and reimbursement criteria by governments, insurers, HMOs, and the like. According to a preferred embodiment, the medical information database 304 is populated with predetermined FFBU qualifying criteria as well as corresponding, previously-obtained medical information for a patient. A patient not meeting the predetermined FFBU qualifying criteria, as determined by schedule processor 302, is not scheduled for an FFBU scan as part of a scheduled x-ray mammogram visit, whereas a patient meeting the FFBU qualifying criteria is scheduled for an FFBU scan on the same clinic visit at which their screening x-ray mammogram is taken, with equipment and personnel schedules being set accordingly. The dotted arrows in FIG. 3 are presented to illustrate that not every patient gets scheduled for an FFBU scan. Preferably, the schedule processor 302 and medical information database 304 comprise portions of a larger hospital information system or radiology information system (HIS/RIS) that automatically perform comparison of the patient data to the predetermined FFBU qualifying criteria. However, in other preferred embodiments the comparison and/or the scheduling can be manual. According to another preferred embodiment, if the patient data meets a predetermined set of higher criteria, termed interest-heightening criteria, the patient is scheduled for a more extensive FFBU scan involving additional compression planes during that same FFBU scanning session.

Because high breast density makes x-ray mammogram screening less effective as a sole modality, the predetermined FFBU qualifying criteria should at least include a previously determined breast density metric for each patient, wherein women having "dense" or "extremely dense" breasts are automatically scheduled for an FFBU scan. Age, patient history data, and a variety of other information may be included such as family medical history, geographic location, demographic information, social information, financial information, and any other factor found to be related to x-ray mammography efficacy, an increase likelihood of breast cancer, and/or the ability for the healthcare institution to get paid and/or reimbursed for the additional procedure.

For clarity of presentation, and by way of a simplified and non-limiting example, the predetermined criteria may be implemented as follows. Any woman having "dense" or "extremely dense" breasts automatically meets the FFBU qualifying criteria. Any woman living in Marin County, California (statistically known to have an abnormally high breast cancer rate), automatically meets the FFBU qualifying criteria, regardless of breast density. Any woman having a prior lumpectomy meets not only the FFBU qualifying criteria but also the interest-heightening criteria and therefore receives a more extensive FFBU scanning session along additional FFBU compression planes. In private clinic settings, any woman having a high financial credit rating and who is a cash-paying customer, not dependent on Medicare or group health insurance, automatically meets the FFBU qualifying criteria, and so on.

Figure 4:
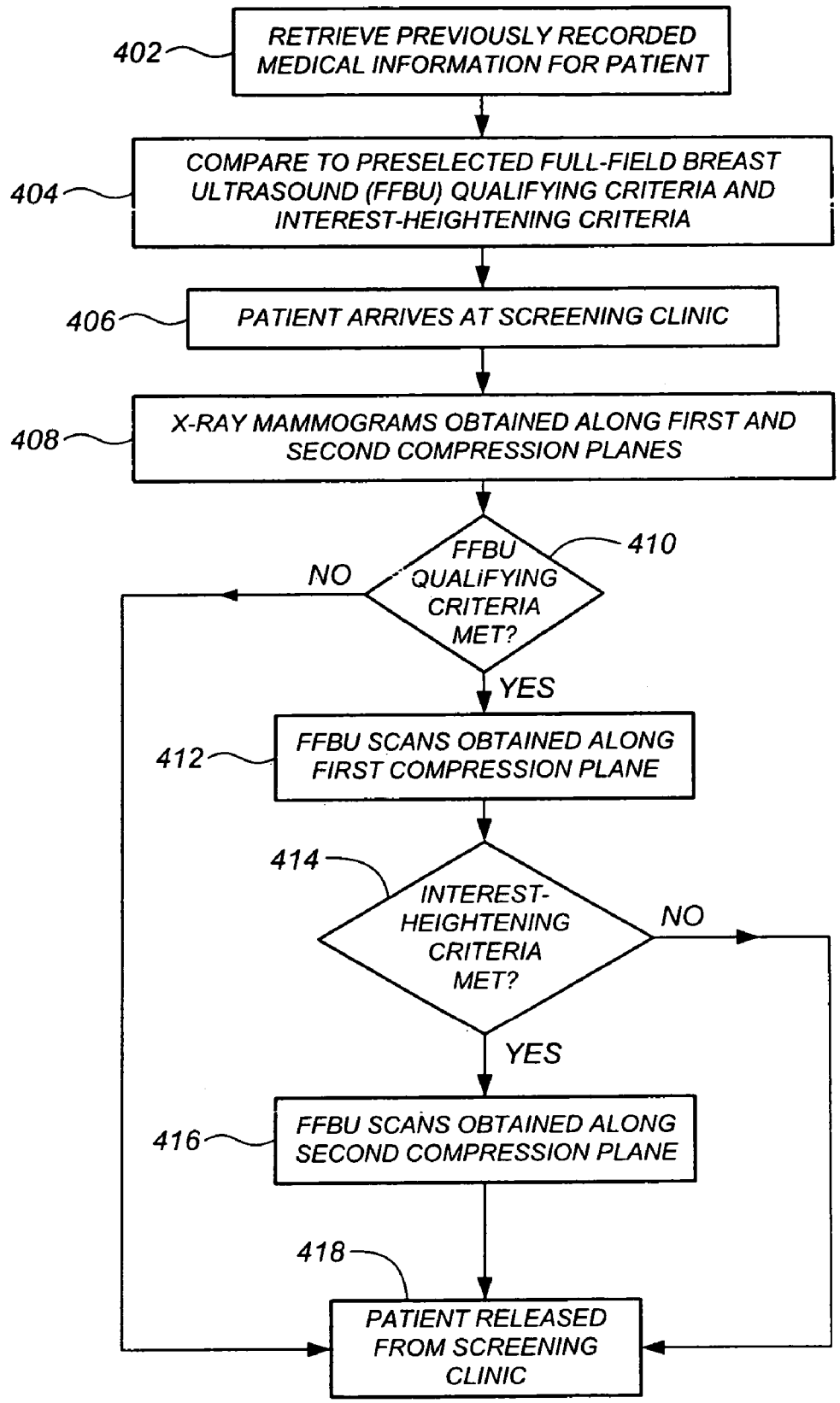
FIG. 4 illustrates workflow steps in an adjunctive full-field breast imaging environment according to a preferred embodiment.

FIG. 4 illustrates workflow steps in an adjunctive full-field breast imaging environment according to a preferred embodiment, comprising a step 402 for retrieving previously recorded medical information for a patient and a step 404 for comparing that information to predetermined FFBU qualifying and interest-heightening criteria. At step 406 the patient arrives at the screening clinic. At step 408, x-ray mammograms are taken, usually according to the standard process of obtaining CC and MLO views for each breast. If the FFBU qualifying criteria are not met (step 410) then the patient is simply released (step 418), but if they are met, then during that same clinic visit FFBU scans are taken of each breast along a first compression plane, preferably a standard x-ray mammogram view plane such as the CC view. If the interest-heightening qualifying criteria are not met (step 414) then the patient is released after the first-compression-plane FFBU scans are obtained (step 418), but if they are met, then the patient is not released until additional FFBU scans are taken of each breast along a second compression plane (step 416), preferably a second standard x-ray mammogram view plane such as the MLO view.

In some cases, it might be deemed necessary to perform an FFBU procedure only after x-ray mammograms have been viewed, in which case the savings of pre-scheduling combined resources are not incurred. However, on the whole, it is expected that a workflow process according to one or more of the above preferred embodiments will reduce overall costs as compared an ad hoc FFBU scheduling process.

Figure 5:
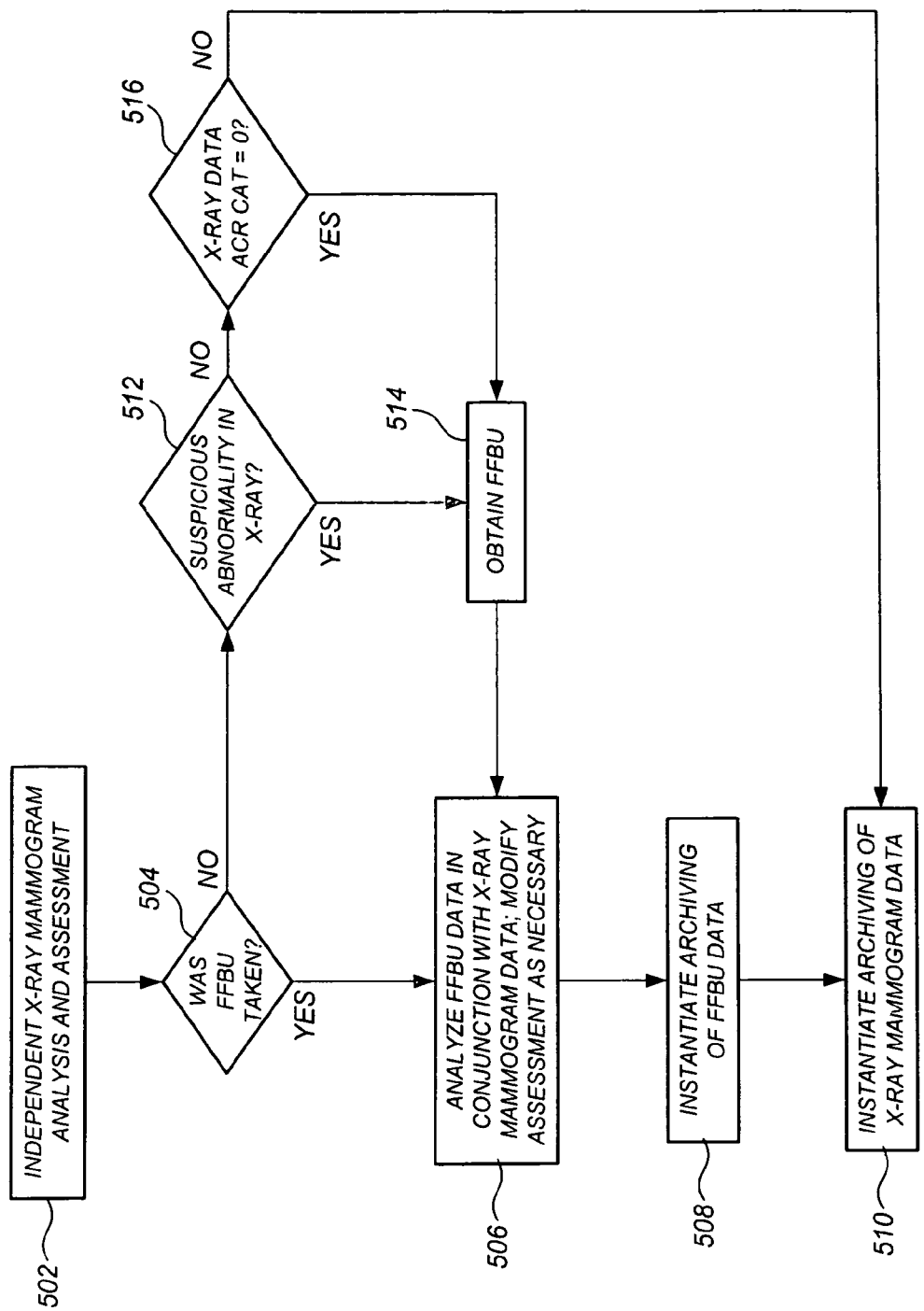
FIG. 5 illustrates a method for viewing and processing breast image data according to a preferred embodiment.

FIG. 5 illustrates a method for viewing and processing breast image data according to a preferred embodiment, presented by way of example and not by limitation. At step 502, x-ray mammogram images are analyzed and assessed independently of data from any other modality, to the extent possible in a sole x-ray mammography environment. This can include viewing x-ray CAD annotations. If at step 504 FFBU scans were taken for this patient, then at step 506 the FFBU data including thick-slice image data is analyzed in conjunction with the x-ray mammogram data, and the assessment is modified as necessary. This can include viewing x-ray CAD annotations, thick-slice image CAD annotations, planar image CAD annotations, volumetric CAD annotations projected onto the thick-slice and/or planar images, and/or joint CAD annotations generated from joint processing of the x-ray and FFBU data projected onto the thick-slice, planar images, and/or x-ray images.

As is well-known in the art, the American College of Radiology has established a breast image assessment standard known as BI-RADS® (Breast Imaging Reporting and Data System) having five assessment categories: Category 1—"negative"; Category 2—"benign finding"; Category 3—"probably benign finding—short interval follow-up suggested"; Category 4—"suspicious abnormality-biopsy should be considered"; and Category 5—"highly suggestive of malignancy—appropriate action should be taken". A sixth category termed Category 0 means that the assessment is incomplete (for any of a variety of reasons) and that further data is needed. Advantageously, at step 506 a suspicious lesion might be discovered even where the x-ray mammogram was evaluated to show no issues at all, for example, what was an ACR BI-RADS Category 1 assessment for x-ray alone could be drastically changed to a Category 4 after the FFBU data is reviewed.

If no FFBU data was acquired, then at step 512 it is determined whether there is a particular amount of suspiciousness falling short of a definite malignancy finding, and perhaps something that would warrant a biopsy procedure or other partially invasive test. This is termed "suspicious abnormality" in the example of FIG. 5, but the scope of the preferred embodiments is not so limited. If present, then an FFBU scan is obtained at step 514. Although this usually involves a patient call-back, it could end up obviating the need for a biopsy procedure or other partially invasive test. Another reason to have an FFBU performed is shown at step 516, if there is a Category 0 assessment that can arise, for example, if the breast was so dense that the x-ray mammogram could really communicate no information at all, or if there was some other problem obtaining an acceptable x-ray mammogram image. However, if it is determined at steps 512 and 516 that there were no problems with the x-ray mammogram image or its contents, then at step 510 the x-ray mammogram data is archived and the breast cancer screening process is complete for that particular visit/session/year.

In one preferred embodiment, the original three-dimensional data volumes, which are not included in the archived dataset, are actively deleted using an affirmative deletion process. In another preferred embodiment, the original three-dimensional data volumes are passively deleted, that is, they are permitted to be maintained on the hard drive(s) associated with the user interface processor 120, where they were last used, until such time as there is no more space to keep them there. Thus, for example, the hard drive associated with the user interface processor 120 may have 1 TB of net storage capacity available as a local cache for maintaining the three-dimensional data volumes for the radiologist viewing sessions. If three-dimensional data volumes have a size of 4 GB for each case, then up to 250 cases can be temporarily stored in the 1 TB cache. After initially filling up 250 cases of data, the cache subsequently overwrites the oldest cases with newly-received cases as they arrive. This arrangement is sometimes referred to as a circular buffer and represents a natural or passive deletion method limited by hardware cost considerations. In this particular example, if 40 patients per day are analyzed, then 25 days' worth of the three-dimensional data is retained. For a given case, after such 25-day period, the three-dimensional data is permanently lost.

In addition to preserving storage space, one foreseeable advantage may lie in the result that the radiologist would only be held legally accountable, in a medical malpractice sense, for only that amount of image data that they were truly able to perceive during the viewing session, i.e., the thick-slice image data. It would arguably be very unfair to hold radiologists legally accountable for entire 4-GB datasets containing hundreds of separate planar images that they do not have the time to individually analyze. Thus, by archiving FFBU data according to the archival datasets of the preferred embodiments and not archiving the entire three-dimensional data volumes, subsequent medical malpractice claims involving unfair hindsight analyses of the entire ultrasound data volumes are avoided, while at the same time a medically sufficient subset of those three-dimensional data volumes is archived to assist in future breast cancer screening for the patients.

Figure 6:
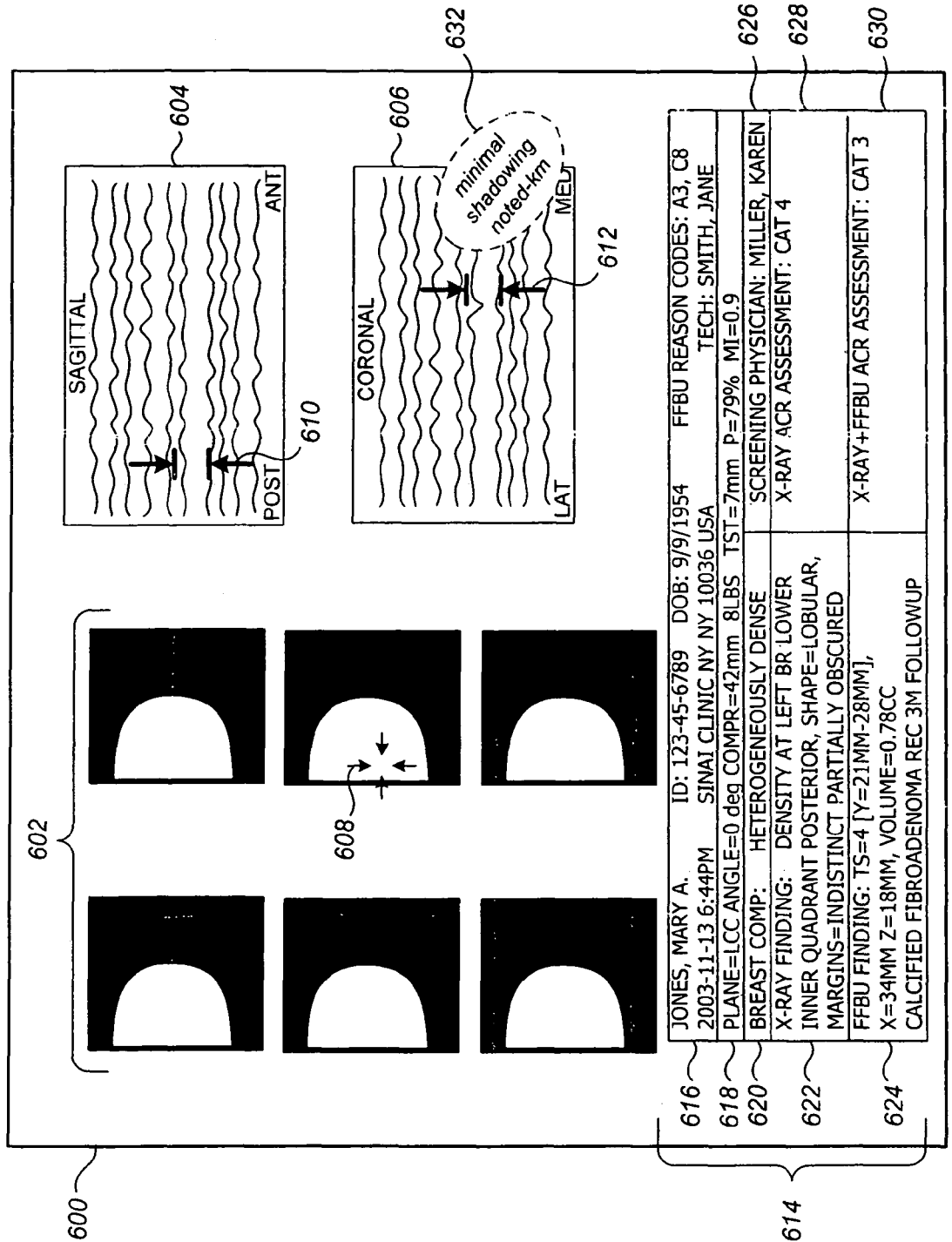
FIGS. 6-9 each illustrate a full-field breast ultrasound (FFBU) archival dataset according to a preferred embodiment.

FIG. 6 illustrates an example of an FFBU archival dataset 600 according to a preferred embodiment. Once again, it is to be appreciated that while the particular "flat-file" expression shown in FIG. 6 is indeed useful in a film-based or paper-based preferred embodiment, as well for generally communicating the features and advantages of the preferred embodiments in the present patent disclosure, the scope of the preferred embodiments extends to many other storage architectures. For example, the different component types such as text comments, 2-D images, annotations, and markers can all be digitally stored in different places, and even on different machines or networks, and associated with hyperlinks.

Archival dataset 600 comprises an array of two-dimensional thick-slice images 602, a first planar view 604, and a second planar view 606. The first planar view 604 corresponds, in this example, to a sagittal plane (parallel to the x-y plane) passing through a location of a finding in the breast that was identified, assessed, and annotated by the viewer during a viewing session. The location of the finding is identified by a finding marker 608, which can be assigned to different shapes, colors, etc. for different kinds of findings and/or assessments. The second planar view 606 corresponds to a coronal plane (parallel to the x-z plane) passing through that location in the breast. Range markers 610 and 612 that were automatically placed on the planar views according to the viewer-selected location on the viewer-selected thick-slice image are also archived as shown. An additional free annotation 632 that was entered by the viewer onto the display using the user interface of the viewing workstation 104 is also archived as shown.

Archival dataset 600 further comprises a text section 614 comprising several components, some automatically generated by the viewing workstation 104 and others being manually entered (via the user interface, dictated, etc.). Text section 614 comprises header information 616 for identifying the patient, clinic, date, and the like, and further including an "FFBU Reason Code" portion that identifies why the patient received the FFBU procedure. These reason codes are preferably related to the FFBU qualifying criteria described supra. By way of example, the "A3" could stand for a geographic indicator (the patient lives in Marin County, for example) and the "C8" could stand for "very dense breasts."

Text section 614 further comprises FFBU-session specific information 618 which can comprise, for example, the compression plane (PLANE=LCC), the associated gantry angle (ANGLE=0 deg), the compression plate distance and force used on the breast (COMPR=42 mm 8 LBS), the thick-slice thickness corresponding to the slab thicknesses (TST=7 mm), an ultrasonic power metric (P=79%, expressed relative to maximum FDA allowable power, and which can alternatively be expressed in absolute units such as $mW/cm^2$), and a mechanical index metric (MI=0.9) indicating a relative potential for mechanical effects and based primarily on the phenomenon of cavitation and considering the biological effects associated with the collapse/implosion of microbubbles.

Text section 614 further comprises a breast composition section 620 that can be automatically supplied (from previously obtained database information) or entered/modified by the FFBU scanning technician or by the viewer/radiologist. The viewer is identified in section 626. Text section 614 further comprises an x-ray finding section 622 and x-ray assessment section 628 corresponding to the determinations at step 502, supra, and an FFBU finding section 624 and x-ray+FFBU assessment section 630 corresponding to additional and/or modified determinations made at step 506, supra. Parts of the FFBU finding section 624 can be completed automatically, for example, the relevant thick-slice (TS=4), location (X=34 MM Z=18 mM), and volume (VOLUME=0.78 CC) corresponding to the finding.

The particular example of FIG. 6 portrays one simplified situation in which there is a cost-saving outcome that is made possible using adjunctive FFBU procedures. In particular, the independent x-ray assessment identified a density with a possibly indistinct border but that was at least partially obscured. The finding was troublesome enough for an ACR Category 4 assessment that might call for an invasive follow-up procedure, such as a fine-needle aspiration (FNA) biopsy, but it would be really useful if more information were quickly available. Advantageously, upon viewing the FFBU thick-slice images, it was readily determined that the lesion was probably a calcified fibroadenoma and could be reassessed to an ACR Category 3. In this case, the invasive and more expensive FNA procedure is avoided, and the patient is simply scheduled for a shorter term (e.g., 3 month) follow-up imaging session to ensure that the size of the probable calcified fibroadenoma is not increasing with time.

According to a preferred embodiment, the thick-slice images 602 correspond to the body of thick-slice images normally presented to the radiologist on the display of the viewing workstation 104. Preferably, the slab-like subvolumes associated with the thick-slice images have an average thickness corresponding to a lesion size to be detected according to the FFBU imaging modality. At an upper end, a larger thickness of 20 mm, for example, may be used if it is desirable to overlook most of the small breast details and direct the user's attention to larger features on the order 10 mm in size. At a lower end, where very high ultrasound resolutions are both desired and available, a smaller thickness of 2 mm, for example, may be used if it is desirable to view small features on the order of 1.3 mm in size. Although a wide range of different thicknesses are within the scope of the preferred embodiments and useful for different purposes, thicknesses in the range of 7 mm-12 mm are likely to be well-suited for most screening and archiving purposes.

Figure 7:
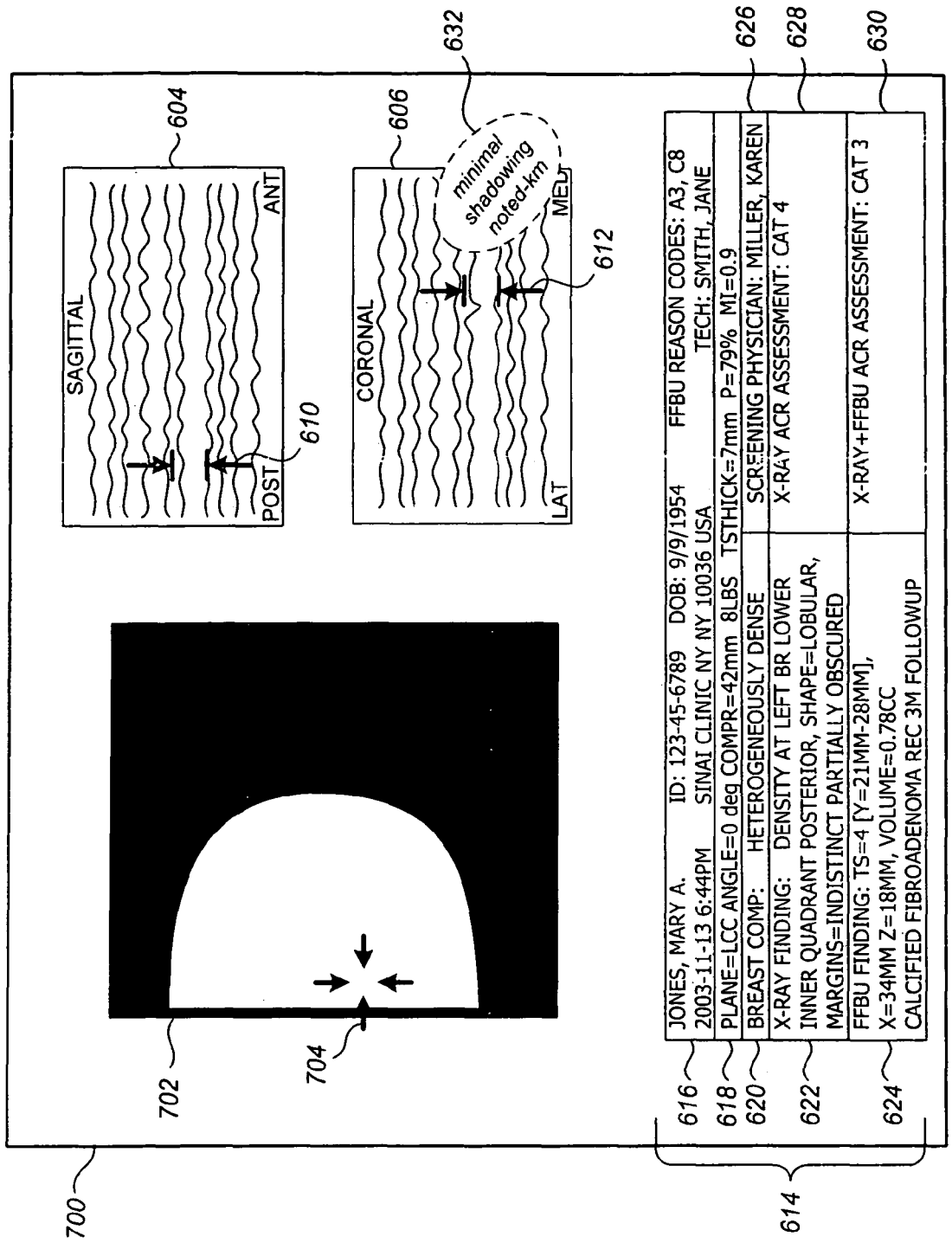

FIG. 7 illustrates an FFBU archival dataset 700 according to a preferred embodiment that is similar to that of FIG. 6 except that a full-size thick-slice image 702 corresponding to the finding is archived. In one preferred embodiment, only those particular thick-slice images containing findings are archived and the remaining thick-slice images are actively or passively discarded. In another preferred embodiment, the archival dataset comprises multiple sheets/records containing the contents of both FIGS. 6 and 7, with additional sheets/records corresponding to FIG. 7 being included for each separate lesion finding. In still another preferred embodiment, in which there are no lesion findings at all, the only image in the archival dataset is a single thick-slice image corresponding to a most benign-looking thick-slice image.

Figure 8:
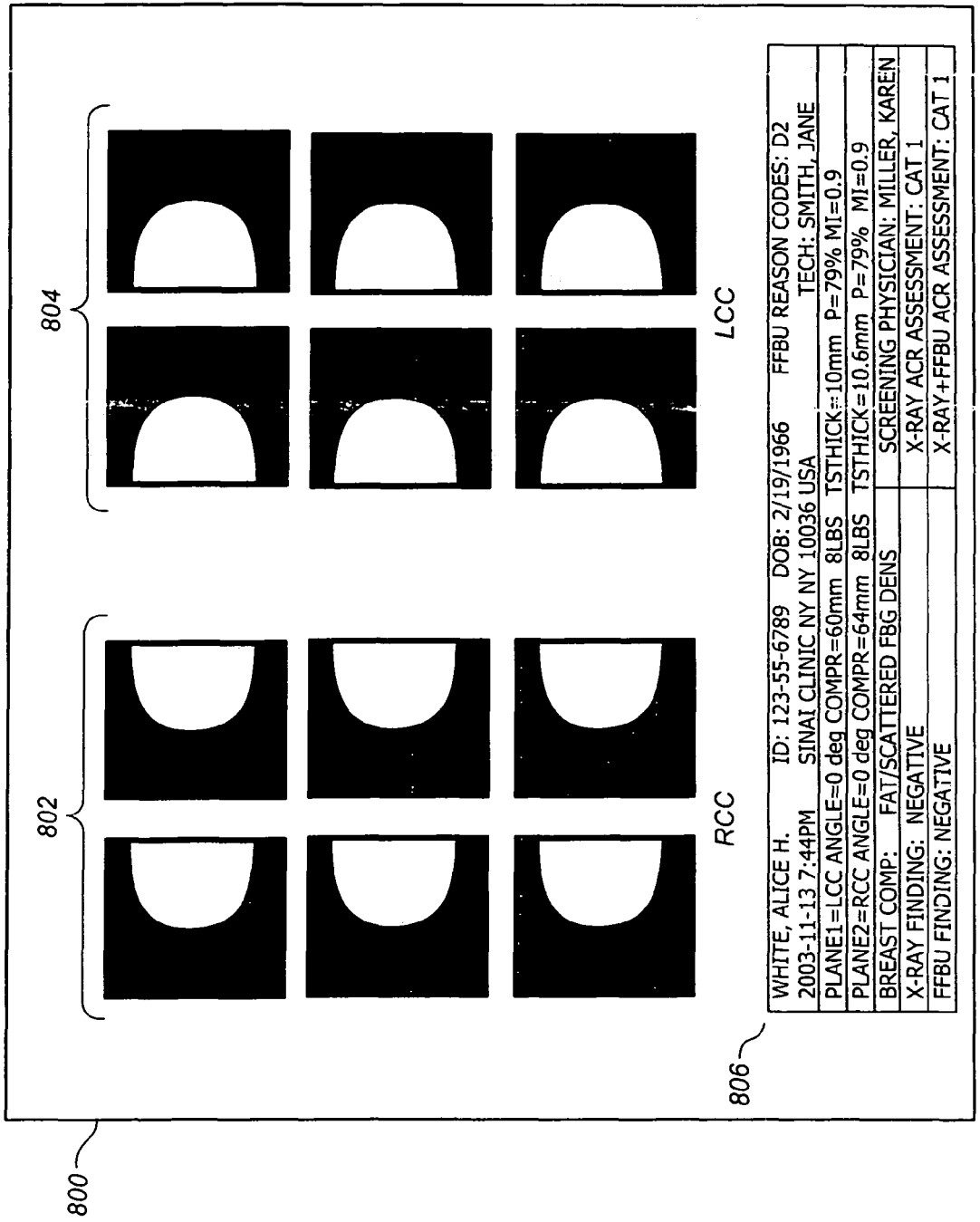

FIG. 8 illustrates an FFBU archival dataset 800 according to a preferred embodiment comprising a first set 802 of thick-slice images corresponding to the RCC view, a second set 804 of thick-slice images corresponding to the LCC view, and a text section 806 similar to the text section 614. The archival dataset 800 is particularly applicable in situations where the FFBU qualifying criteria were met and the interest-heightening criteria were not met. In such case, FFBU scanning is only scheduled for a single compression plane such as the CC plane for each breast. If the x-ray mammogram and FFBU data both look good to the viewer (e.g., Category 1), the archival dataset 800 is formed and archived. If one or more findings are present, additional sheets/records corresponding to FIG. 6 or 7 are included in the archive dataset.

Figure 9:
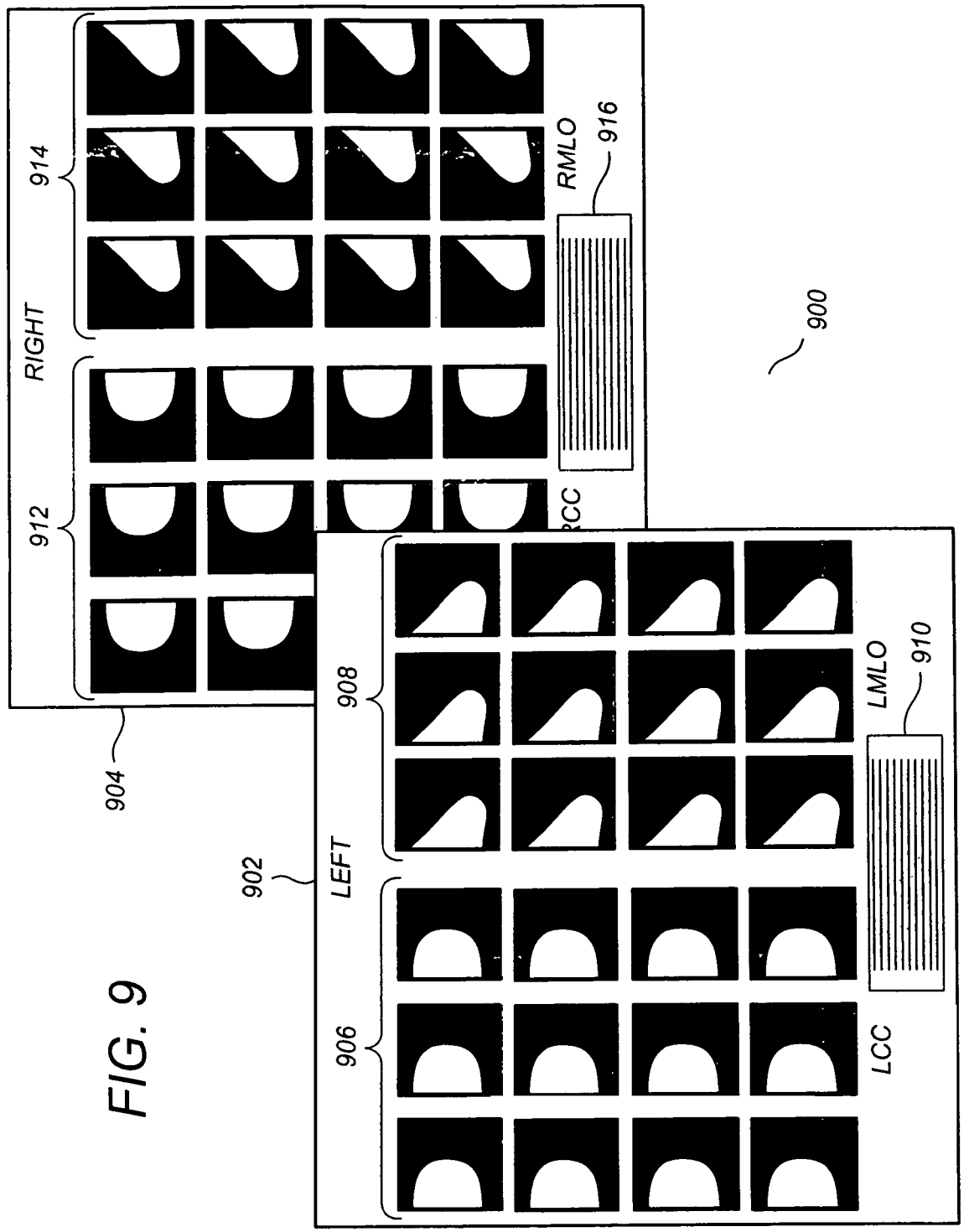

FIG. 9 illustrates an FFBU archival dataset 900 according to a preferred embodiment comprising a first sheet/record 902 having CC and MLO thick-slice image datasets 906 and 908, respectively, for the left breast and a second sheet/record 904 having CC and MLO thick-slice image datasets 912 and 914, respectively, for the right breast. Text sections 910 and 916 are also included similar to text sections 806/614 supra. The archival dataset 900 is particularly applicable in situations where both the FFBU qualifying criteria and the interest-heightening criteria were met. In such case, more extensive FFBU scanning is scheduled having at least one additional compression plane, such as an MLO plane, for each breast. If the x-ray mammogram and FFBU data both look good to the viewer (e.g., Category 1), the archival dataset 900 is formed and archived. If one or more findings are present, additional sheets/records corresponding to FIG. 6 or 7 are included in the archive dataset.

Notably, the preferred embodiments of FIGS. 8 and 9 are particularly advantageous in the event of a possible, but not yet actuated, change in government regulations and/or standard clinical procedures in which younger women, under the age of 40 for example, are to be regularly screened for breast abnormalities. In such a case, it would be desirable not to use x-ray mammography at all as part of the screening process because of the x-ray dosages involved which are cumulative over the patient's entire lifetime. Rather, only a non-x-ray based full-field modality, such as FFBU screening or MRI screening, is mandated. In such cases, the presentation of the thick-slice image data to radiologists and archiving of the radiologist-viewed thick-slice images according to the archive datasets of FIGS. 8 and 9 would be particularly useful.

Figure 10:
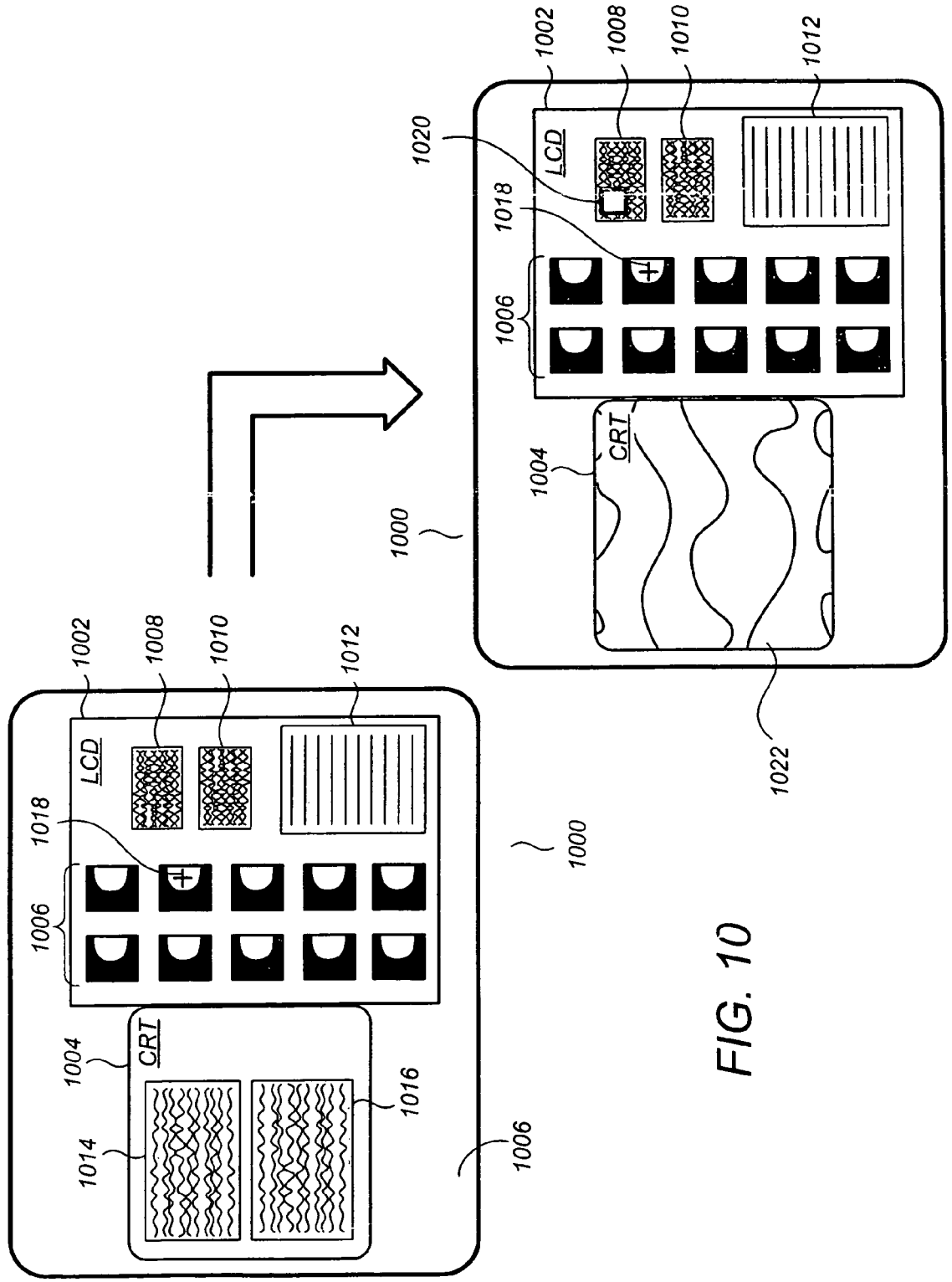
FIG. 10 illustrates a display of an FFBU viewing workstation according to a preferred embodiment.

FIG. 10 illustrates a display of an adjunctive FFBU display 1000 according to a preferred embodiment that can be integrated into the viewing workstation 104, supra. A CRT monitor 1004 and an LCD monitor 1002 are packaged in a plastic frame case 1006 which provides support and electrical safety protection. The FFBU display 1000 can be mounted on a swayable arm so as to be movable close to displayed X-ray film and/or softcopy workstation displays. It can also be mounted on a film viewer table as shown in FIG. 1, which is a preferred configuration because radiologists do not have to swing their heads left to right to review X-Ray film and FFBU images. The LCD monitor 1002 displays thick-slice images 1006, planar images 1008, and relevant text data 1012 as needed. One or both of the planar images 1008 and 1010 can be shown at full-scale. The CRT display 1004 also displays planar ultrasound views 1014 and 1016. The planar ultrasound views correspond to a cursor location 1018 on the thick-slice images.

In general, each display device has its own display property. Gamma correction for each monitor is required when image data from the same source output to different display device. Since current invention uses two or more monitors, separate gamma corrections are required. Commercially available graphic display cards provide two or more video outputs and Gamma corrections for each video output. This is an economic way to implement. Otherwise, two or more separate graphic display cards can be used, which provide separate Gamma corrections.

According to a preferred embodiment, the FFBU display 1000 facilitates an image enlargement procedure. When the viewer enables a zoom function, a virtual ROI 1020 box is established according to a default setting (e.g., size, location). The viewer can use a computer trackball or mouse to resize or move the location of virtual ROI box 1020. The ultrasound image data is re-scan-converted and displayed based on the virtual ROI box location, dimensions, and/or other specifications. A zoomed version 1022 of the virtual ROI 1020 is displayed on CRT monitor 1004.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, while described above primarily in terms of using several thick-slice images in the archival dataset to represent the clinically relevant breast volume for a particular view, in an alternative preferred embodiment there can be a single overall thick-slice image used to represent the ultrasound data volume. Preferably, this single overall thick-slice image is "intelligently" computed from the three-dimensional dataset in a manner that highlights lesions that may be contained in the breast using, for example, one or more of the computational methods described in U.S. Ser. No. 10/305,661 and U.S. Ser. No. 60/439,437, supra. Therefore, references to the details of the preferred embodiments are not intended to limit their scope, which is limited only by the scope of the claims set forth below.

What is claimed is:

1. A system for processing medical image data corresponding to a breast, comprising:
    a source of a three-dimensional data volume representing at least one physical property within the breast;
    a processor coupled with said source to receive said three-dimensional data volume to compute therefrom a two-dimensional thick-slice image representing said at least one physical property of the breast in a slab-like subvolume thereof;
    a display coupled with said processor and displaying said thick-slice image to a viewer;
    an archiving device coupled with said processor to receive said two-dimensional thick-slice image, said archiving device generating an archival dataset including said two-dimensional thick-slice image, said archiving device transferring said archival dataset to a tangible storage medium for archiving purposes;
    said display further displaying a two-dimensional planar view image corresponding to said at least one physical property along a planar slice within the breast, wherein said archival dataset further comprises said two-dimensional planar image;
    wherein said at least one physical property is a sonographic property, and wherein said three-dimensional data volume is not included in said archival dataset thereby promoting archival efficiency in said archiving device.

2. The system of claim 1, wherein said system passively discards said three-dimensional data volume in a circular buffer arrangement, and wherein said tangible storage medium is selected from the group consisting of: paper, film, magnetic disk, optical disk, magnetic tape, and non-volatile integrated circuit memory.

3. A system for processing medical image data corresponding to a breast, comprising:
    a source of a three-dimensional data volume representing at least one physical property within the breast;
    a processor coupled with said source to receive said three-dimensional data volume to compute therefrom a two-dimensional thick-slice image representing said at least one physical property of the breast in a slab-like subvolume thereof;
    a display coupled with said processor and displaying said thick-slice image to a viewer;
    an archiving device coupled with said processor to receive said two-dimensional thick-slice image, said archiving device generating an archival dataset including said two-dimensional thick-slice image, said archiving device transferring said archival dataset to a tangible storage medium for archiving purposes;
    said display further displaying a two-dimensional planar view image corresponding to said at least one physical property along a planar slice within the breast, wherein said archival dataset further comprises said two-dimensional planar image; and
    a user input device receiving a first viewer input identifying on said thick-slice image a location of interest in the breast, wherein said planar view image corresponds to a planar slice passing through that location of interest in the breast;
    said user input device further receiving a second viewer input identifying said location of interest for archiving, wherein said archival dataset includes the thick-slice image and the planar view image corresponding to that location of interest.

4. The system of claim 3, said user input device further receiving a third viewer input requesting lesion volume information for said location of interest, said display providing said lesion volume information to the viewer responsive to said third viewer input.

5. A system for processing medical image data corresponding to a breast, comprising:
   a source of a three-dimensional data volume representing at least one physical property within the breast;
   a processor coupled with said source to receive said three-dimensional data volume to compute therefrom a two-dimensional thick-slice image representing said at least one physical property of the breast in a slab-like subvolume thereof;
   a display coupled with said processor and displaying said thick-slice image to a viewer;
   an archiving device coupled with said processor to receive said two-dimensional thick-slice image, said archiving device generating an archival dataset including said two-dimensional thick-slice image, said archiving device transferring said archival dataset to a tangible storage medium for archiving purposes;
   said display further displaying a two-dimensional planar view image corresponding to said at least one physical property along a planar slice within the breast, wherein said archival dataset further comprises said two-dimensional planar image; and
   a user input device receiving a first viewer input identifying on said thick-slice image a location of interest in the breast, wherein said planar view image corresponds to a planar slice passing through that location of interest in the breast;
   said user input device further receiving a second viewer input identifying said location of interest for archiving, wherein said archival dataset includes the thick-slice image corresponding to that location of interest but does not include the planar view image corresponding to that location of interest.

6. A system for processing medical image data corresponding to a breast, comprising:
   a source of a three-dimensional data volume representing at least one physical property within the breast;
   a processor coupled with said source to receive said three-dimensional data volume to compute therefrom a two-dimensional thick-slice image representing said at least one physical property of the breast in a slab-like subvolume thereof;
   a display coupled with said processor and displaying said thick-slice image to a viewer; and
   an archiving device coupled with said processor to receive said two-dimensional thick-slice image, said archiving device generating an archival dataset including said two-dimensional thick-slice image, said archiving device transferring said archival dataset to a tangible storage medium for archiving purposes;
   said processor computing additional two-dimensional thick-slice images corresponding to different slab-like subvolumes of the breast to form a set of thick-slice images, said slab-like subvolumes for said set of thick-slice images collectively occupying substantially all of a clinically relevant portion of the breast volume, said display displaying each of said set of thick-slice images to the viewer;
   said archival dataset including each of said set of thick-slice images;
   wherein said slab-like subvolumes have an average thickness roughly equal to about 0.5-3.0 times an expected size of lesions L to be detected according to an imaging modality of said medical image data.

7. The system of claim 6, wherein said imaging modality is ultrasound, and wherein said slab-like volumes have an average thickness lying between about 2 mm and 20 mm.

8. The system of claim 6, said display further displaying a two-dimensional planar view image corresponding to said at least one physical property along a planar slice within the breast, said system further comprising a user input device receiving a first viewer input identifying on a first of said set of thick-slice images a first location of interest in the breast, wherein said planar view image corresponds to a planar slice passing through said first location of interest in the breast.

9. The system of claim 8, said archival dataset comprising a first annotation for said first thick-slice image identifying said first location of interest thereon, said archival dataset further comprising said planar view image corresponding to said first location of interest, said archival dataset being configured to facilitate simultaneous, side-by-side viewing of said first thick-slice image, said first annotation, and said planar view image corresponding to said first location of interest.

10. The system of claim 9, said archival dataset being configured to facilitate simultaneous, side-by-side viewing of (i) said first thick-slice image including said first annotation, (ii) said planar view image corresponding to said first location of interest, and (iii) all remaining members of said set of thick-slice images.

11. The system of claim 10, said user input device receiving a second viewer input identifying a second location of interest in the breast, said archival dataset further configured to facilitate simultaneous, side-by-side viewing of (i) a thick-slice image from said set of thick-slice images upon which said second location of interest in the breast was identified, (ii) a second annotation received corresponding to said second location of interest, and (iii) a planar view image corresponding to said second location of interest.

12. The system of claim 6, said processor further processing said three-dimensional data to detect anatomical abnormalities in the breast, said display annotating each thick-slice image associated with at least one detected abnormality to identify thereon a location of said at least one detected abnormality, wherein said archival dataset comprises at least each of said annotated thick-slice images and each of said associated annotations.

13. The system of claim 12, said system being further configured to prevent the viewer from dissociating any of said annotations with associated thick-slice image.

14. A system for processing medical image data corresponding to a breast, comprising:
   a source of a three-dimensional data volume representing at least one physical property within the breast;
   a processor coupled with said source to receive said three-dimensional data volume to compute therefrom a two-dimensional thick-slice image representing said at least one physical property of the breast in a slab-like subvolume thereof;
   a display coupled with said processor and displaying said thick-slice image to a viewer; and
   an archiving device coupled with said processor to receive said two-dimensional thick-slice image, said archiving device generating an archival dataset including said two-dimensional thick-slice image, said archiving device transferring said archival dataset to a tangible storage medium for archiving purposes;

said processor computing additional two-dimensional thick-slice images corresponding to different slab-like subvolumes of the breast to form a set of thick-slice images, said slab-like subvolumes for said set of thick-slice images collectively occupying substantially all of a clinically relevant portion of the breast volume, said display displaying each of said set of thick-slice images to the viewer;

said system further comprising a user input device receiving a viewer input identifying, in the event that the viewer has found no interesting locations in the breast, a most benign-looking one of said set of thick-slice images for archiving, said archival dataset including said most benign-looking one of said set of thick-slice images, said system dissociating said three-dimensional data volume and all others of said set of thick-slice images from said dataset.

15. The system of claim 14, wherein said three-dimensional data volume and said others of said set of thick-slice images are dissociated in a passive deletion process including a circular buffer arrangement.

16. A method, comprising:
receiving a three-dimensional data volume representing at least one physical property within a breast;
computing from said three-dimensional data volume a two-dimensional thick-slice image representing said at least one physical property in a slab-like subvolume of the breast;
displaying said two-dimensional thick-slice image to a viewer in conjunction with at least one x-ray mammogram image of the breast;
generating an archival dataset including said two-dimensional thick-slice image and including data that associates said two-dimensional thick-slice image with said at least one x-ray mammogram image; and
displaying a two-dimensional planar view image corresponding to said at least one physical property along a planar slice within the breast, said archival dataset further including said two-dimensional planar image;
wherein said at least one physical property is a sonographic property, and wherein said slab-like subvolume has a thickness in the range of 2 mm-20 mm.

17. The method of claim 16, further comprising transferring said archival dataset to a tangible storage medium selected from the group consisting of: paper, film, magnetic disk, optical disk, magnetic tape, and non-volatile integrated circuit memory.

18. The method of claim 16, further comprising receiving a first viewer input identifying on said thick-slice image a location of interest in the breast, wherein said planar view image corresponds to a planar slice passing through that location of interest in the breast.

19. The method of claim 18, further comprising receiving a second viewer input identifying said location of interest for archiving, wherein said archival dataset includes the thick-slice image and the planar view image corresponding to that location of interest.

20. The method of claim 19, further comprising:
receiving a third viewer input requesting lesion volume information for said location of interest;
automatically segmenting a lesion centered near said location of interest;
automatically computing a lesion volume metric corresponding to the segmented lesion; and
displaying said lesion volume metric to the viewer.

21. The method of claim 19, further comprising:
generating additional two-dimensional thick-slice images corresponding to different slab-like subvolumes of the breast to form a set of thick-slice images, said slab-like subvolumes for said set of thick-slice images collectively occupying substantially all of a clinically relevant portion of the breast volume;
displaying each of said set of thick-slice images to the viewer; and
including each of said set of thick-slice images in said archival dataset.

* * * * *